US008241208B2

(12) United States Patent
Jiang et al.

(10) Patent No.: US 8,241,208 B2

(45) Date of Patent: Aug. 14, 2012

(54) ENDOSCOPE DISPOSABLE SHEATH

(76) Inventors: Kerang Jiang, Shenyang (CN); Shoumei Jiang, Shenyang (CN)

( * ) Notice: Subject to any disclaimer, the term of this patent is extended or adjusted under 35 U.S.C. 154(b) by 97 days.

(21) Appl. No.: 12/793,947

(22) Filed: Jun. 4, 2010

(65) Prior Publication Data

US 2011/0251460 A1 Oct. 13, 2011

(30) Foreign Application Priority Data

Apr. 9, 2010 (CN) .......................... 2010 1 0162668

(51) Int. Cl.
*A61B 1/12* (2006.01)
*A61B 1/04* (2006.01)

(52) U.S. Cl. ........ 600/159; 600/121; 600/123; 600/156; 600/158

(58) Field of Classification Search .......... 600/121–125, 600/154–159, 131, 132, 133–134; 356/241.1–241.6
See application file for complete search history.

(56) References Cited

U.S. PATENT DOCUMENTS 4,537,182 A * 8/1985 Otani ............................ 600/159
4,694,821 A * 9/1987 Kondo .......................... 600/158
4,809,679 A * 3/1989 Shimonaka et al. .......... 600/154
5,050,585 A * 9/1991 Takahashi ..................... 600/123
5,201,908 A * 4/1993 Jones ............................ 600/123
5,518,501 A * 5/1996 Oneda et al. .................. 600/127
5,695,449 A * 12/1997 Moriyama ..................... 600/122
5,993,380 A * 11/1999 Yabe et al. ..................... 600/121
2003/0097043 A1* 5/2003 Ouchi et al. .................. 600/122
2008/0249362 A1* 10/2008 Jiang et al. .................... 600/121

* cited by examiner

*Primary Examiner* — Matthew J Kasztejna
*Assistant Examiner* — Ryan Henderson
(74) *Attorney, Agent, or Firm* — Matthias Scholl P.C.; Matthias Scholl

(57) ABSTRACT

A disposable protecting cover for an endoscope, the endoscope comprising a endoscope and a disposable valve disk, and the disposable protecting cover comprising a disposable sheath, a clamping tube, a disposable suction tube, a three-way sealing cap, a water air tube, and a protecting cover comprising a hand entrance and an instrument insertion opening. A support ring is disposed in the front of the disposable sheath, a convex portion and a concave portion are respectively disposed on both sides of the support ring and fit with a concave portion and a convex portion on a head of the endoscope, the water air tube is connected to the disposable sheath, a one-way valve is disposed on the water air tube and outside the disposable sheath, the protecting cover is in the shape of a cap and made of transparent film, the protecting cover operates to cover an operating portion of the endoscope of the endoscope, the instrument insertion portion is elastically fit with an upper opening of the three-way sealing cap, a suck-in connector and a suck-out connector are disposed on a valve seat of the disposable valve disk, and connected to the disposable suction tube, and the suck-in connector, the suck-out connector, and the disposable suction tube are dispose outside the endoscope.

8 Claims, 9 Drawing Sheets

5.2 5.1 5 4 6 3 5.4 3.1 1.6 7 1.7 1.2 6 1 1.5 2.6 2.7 2.3 1.3 2.5 1.4 2.4 1.1 2 A B C D 2.1 2.2

ENDOSCOPE DISPOSABLE SHEATH

CROSS-REFERENCE TO RELATED APPLICATIONS

Pursuant to 35 U.S.C. §119 and the Paris Convention Treaty, the invention claims the benefit of Chinese Patent Application No. 201010162668.8 filed on Apr. 9, 2010, the contents of which are incorporated herein by reference.

BACKGROUND OF THE INVENTION

1. Field of the Invention

The invention relates to a medical device, and more particularly to a disposable protecting cover for an endoscope.

2. Description of the Related Art

An endoscope is widely used to go deeply into a cavity of a patient for examination and operation in medical field. The endoscope comprises an insertion portion disposed in the front thereof, comprising a viewing system, an illumination system, an operating system, a biopsy channel, a water air tube and a suction tube, the insertion portion having a 1-2 meter flexible cylinder, an operating portion disposed in the middle thereof, and a light guide portion disposed at the back thereof and connected to a light resource, an image processor, a water vapor pump, and a suction machine and so on. The endoscope contacts with a endoscope cavity, endoscope fluid and blood, so strict disinfection is required. Due to materials and structure of the endoscope, it cannot be disinfected by steam at high temperature and pressure, and as the high cost thereof, it cannot be used for only one time like an injector or a cardiac catheter. To facilitate disinfection, washing via disinfectant solution and dipping not only cost large amount of water and electricity, but also require sewage treatment, and disinfectant effect thereof is not stable enough. In order to improve the reliability of the endoscope disinfection, several methods are disclosed in US patents for overcoming the problem thereof.

To overcome the above-mentioned problems, an endoscope with a sheath is used. However, there are several disadvantages with the endoscope: firstly, a suction tube is disposed in a endoscope of the endoscope and cannot be changed after use, which makes it the most polluted and unsafe; secondly, there is no fixing device between the front of a sheath and a head of the endoscope, which may cause one of them to detach from the other; thirdly, no one-way valve is disposed on a water air tube to prevent backstreaming, which causes water or air to flow reversely as pressure in a cavity of a patient varies; fourthly, an operating portion of the endoscope is not covered and protected, and may be contaminated by hands of a doctor; fifthly, though a prior art (such as U.S. Pat. No. 6,852,772 B2) discloses a method for protecting the operating portion, materials and structure of the endoscope are not practical, and production cost thereof is high.

SUMMARY OF THE INVENTION

In view of the above-described problem, it is one objective of the invention to provide a disposable protecting cover for an endoscope that is capable of addressing the above-mentioned problems.

To achieve the above objectives, in accordance with one embodiment of the invention, provided is a disposable protecting cover for an endoscope, the endoscope comprising a endoscope and a disposable valve disk, and the disposable protecting cover comprising a disposable sheath, a clamping tube, a disposable suction tube, a three-way sealing cap, a water air tube, and a protecting cover comprising a hand entrance and an instrument insertion opening. A support ring is disposed in the front of the disposable sheath, a convex portion and a concave portion are respectively disposed on both sides of the support ring and fit with a concave portion and a convex portion on a head of the endoscope, the water air tube is connected to the disposable sheath, a one-way valve is disposed on the water air tube and outside the disposable sheath, the protecting cover is in the shape of a cap and made of transparent film, the protecting cover operates to cover an operating portion of the endoscope of the endoscope and other portions thereof that are not covered by the sheath, the instrument insertion opening is elastically fit with an upper opening of the three-way sealing cap, a suck-in connector and a suck-out connector are disposed on a valve seat of the disposable valve disk, and connected to the disposable suction tube, and the suck-in connector, the suck-out connector, and the disposable suction tube are disposed outside the endoscope.

In a class of this embodiment, an arch-shaped cavity is disposed at the center of the instrument insertion opening.

In a class of this embodiment, the arch-shaped cavity protrudes inwards.

In a class of this embodiment, a cut that can be opened is disposed at the center of the arch-shaped cavity.

Advantages of the invention comprise:

1. the convex portion and the concave portion are respectively disposed on both sides of the support ring and fit with the concave portion and the convex portion on the head of the endoscope, which makes installation of the suction convenient and practical;

2. the suction tube and the suction valve are disposed outside the endoscope of the endoscope, and can be changed after use, which improve reliability of disinfection;

3. the one-way valve disposed on the water air tube and outside the disposable sheath prevents backstreaming in the water air tube, and thus cross infection among different patients;

4. the disposable protecting cover of the invention enables a reusable endoscope to have reliable disinfecting effect, reduces disinfecting time, increases work life of the endoscope of the endoscope, saves a large amount of water and electricity, and cost spent on processing medical sewage, implements energy conservation and emission reduction, reduces the number of the endoscopes used in hospitals and corresponding cost, and protects environment.

Comparing with U.S. Pat. No. 6,852,077 B2, the coronary transparent film cover has some advantages as follows:

a. The invention is coronary, and can cover the outer surface of the operating portion and other portions near the operating portion from the top to the bottom and has an opening facing downwards, in a manner of wearing a cap; while in the FIGS. 1-13 of the U.S. Pat. No. 6,852,077 B2, it covers the operating portion from the bottom to the top, that is, from 102 to the top, in a manner of wearing trousers, and the big opening 103a covers the light guide portion and the doctor's left hand. In addition, in the FIGS. 15, 16, 29, and 30, the cover covers the outer surface of the endoscope operating portion, and closes it, and does not protect the operator's hand.

b. The invention is made of transparent film and easy for observation, and features light weight, low cost and so on. These materials enable the heat seal forceps to align with the hole of the three-way sealing cap, and to cut off the disposable forceps channel; while in the U.S. Pat. No. 6,852,077 B2, it uses high polymer annular elastic materials that do not have the above advantages of the invention, in addition, it is not elastic.

c. The cover is fixed on the endoscope by connecting the instrument insertion opening to the three-way sealing cap, which makes it easy for installing and detaching. While in FIGS. 22 and 23 of U.S. Pat. No. 6,852,077 B2, the water air valve connects the suction valve; the position of 441 and 442 is near, but the connection method is different. The instrument insertion opening of the invention is a component with protection film, while in U.S. Pat. No. 6,852,077 B2, the cover is disposed on the endoscope 441 first, then, 442 is disposed on it, obviously it has essential difference from the invention. As for FIGS. 27, 28 in the FIG. 27, the connection has no feasibility; in addition, as shown in FIG. 13, the operator's left hand is not in the cover, so it cannot be protected and is unsafe.

d. The instrument insertion opening has two purposes: firstly makes it convenient for fixing the cover on the endoscope. The instrument insertion opening is elastically connected to the three-way sealing cap, so installation and detachment are very easy, in a manner of pressing and releasing a button on clothes, and it is better than the method in U.S. Pat. No. 6,852,077 B2. Secondly, because of the arched endoscope and close cut in the instrument insertion opening, as the instruments is inserted or taking out, the contaminant cannot be discharged from the three-way sealing cap. After use, the disposable suction tube, disposable valve disk, coronary transparent film protection cover and the three-way sealing cap can be removed as a whole part. This is very convenient, and improves the reliability of disinfection. In addition, the invention features low cost, and is easy to operate and promote.

In which: 1—endoscope, 1.1—endoscope insertion portion, 1.2—endoscope operating portion, 1.3—endoscope light guide portion, 1.4—endoscope channel, 1.5—endoscope upper opening, 1.6—suction valve seat, 1.7—endoscope water air tube connector, 2—sheath, 2.1—support ring, 2.2—nozzle, 2.3—disposable suction tube, 2.4—locking ring, 2.5—disposable water air tube, 2.6—disposable water air connector, 2.7—one-way valve, 3—three-way sealing cap, 3.1—heat seal hole, 3.2—following sealing ring, 3.3—suction connector, 3.4—three-way sealing cap upper opening, 3.5—endoscope connector, 4—disposable valve disk, 4.1—valve core, 4.2—valve seat, 4.3—spring, 4.4—sealing packing, 4.5—sealing sheath, 4.6—suck-in connector, 4.7—suck-out connector, 4.8—long opening, 4.9—suck-in hole, 4.10—compressing portion, 4.11—upper central opening, 4.12—fixing hook, 5—protecting cover, 5.1—instrument insertion opening, 5.2—hand entrance, 5.3—arch-shaped cavity, 5.4—cover lower opening (big opening), 5.5—trisection cut, 5.6—quartering cut, 6—suction tube, 7—flexible clip, 8—heat seal forceps

DETAILED DESCRIPTION OF THE EMBODIMENTS

Further description of the invention will be given below in conjunction with accompanying drawings and specific embodiments.

Figure 1:
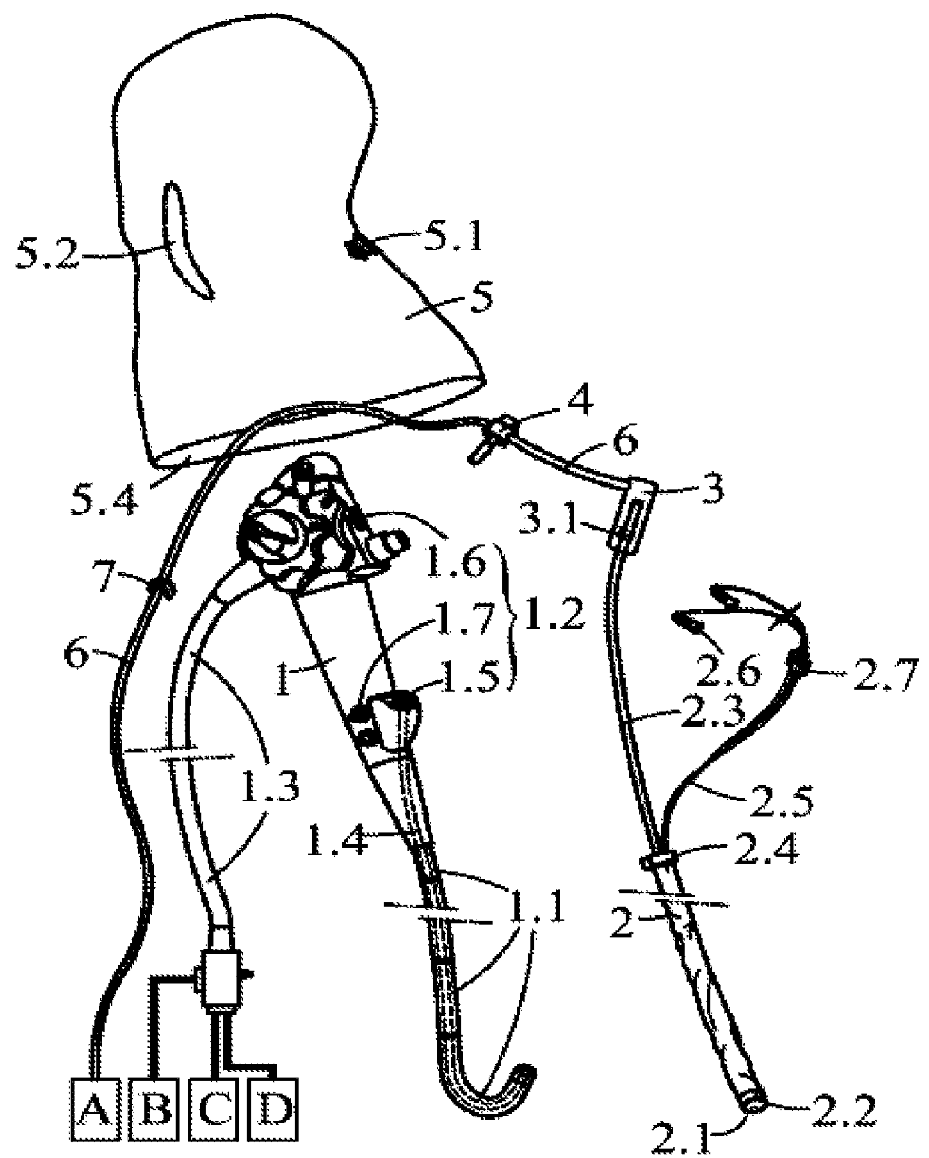
FIG. 1 illustrates a disposable protecting cover for an endoscope and an endoscope.
Figure 2:
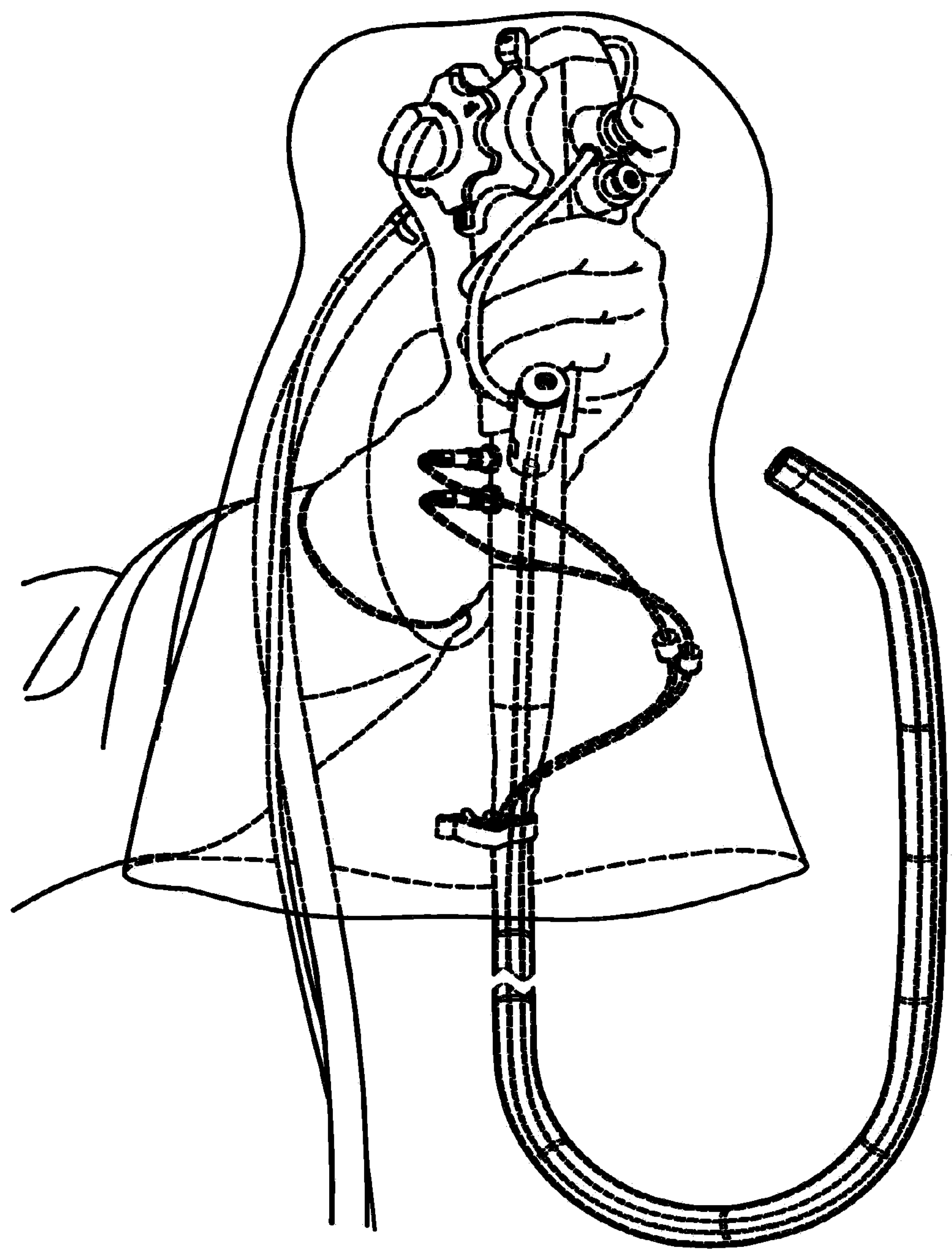
FIG. 2 illustrates a disposable protecting cover for an endoscope and an endoscope connected altogether.
Figure 3:
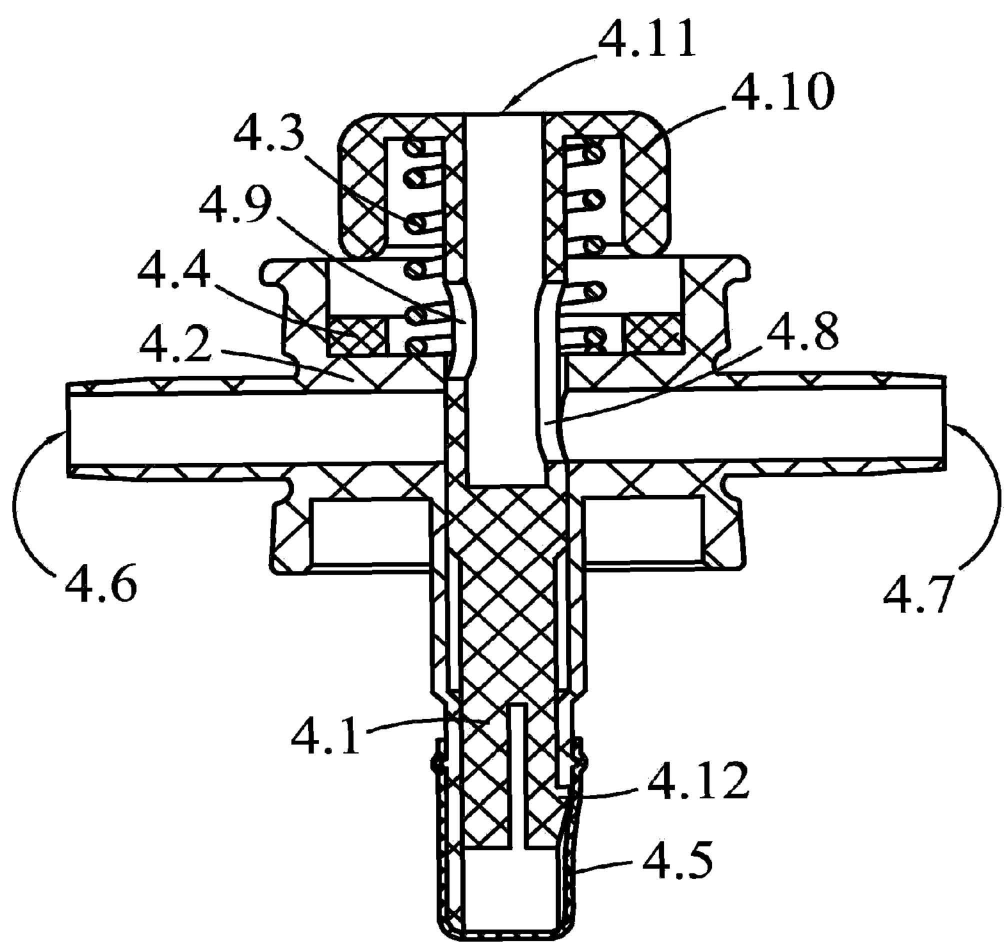
FIG. 3 is a schematic view of a disposable valve disk of the invention.
Figure 4:
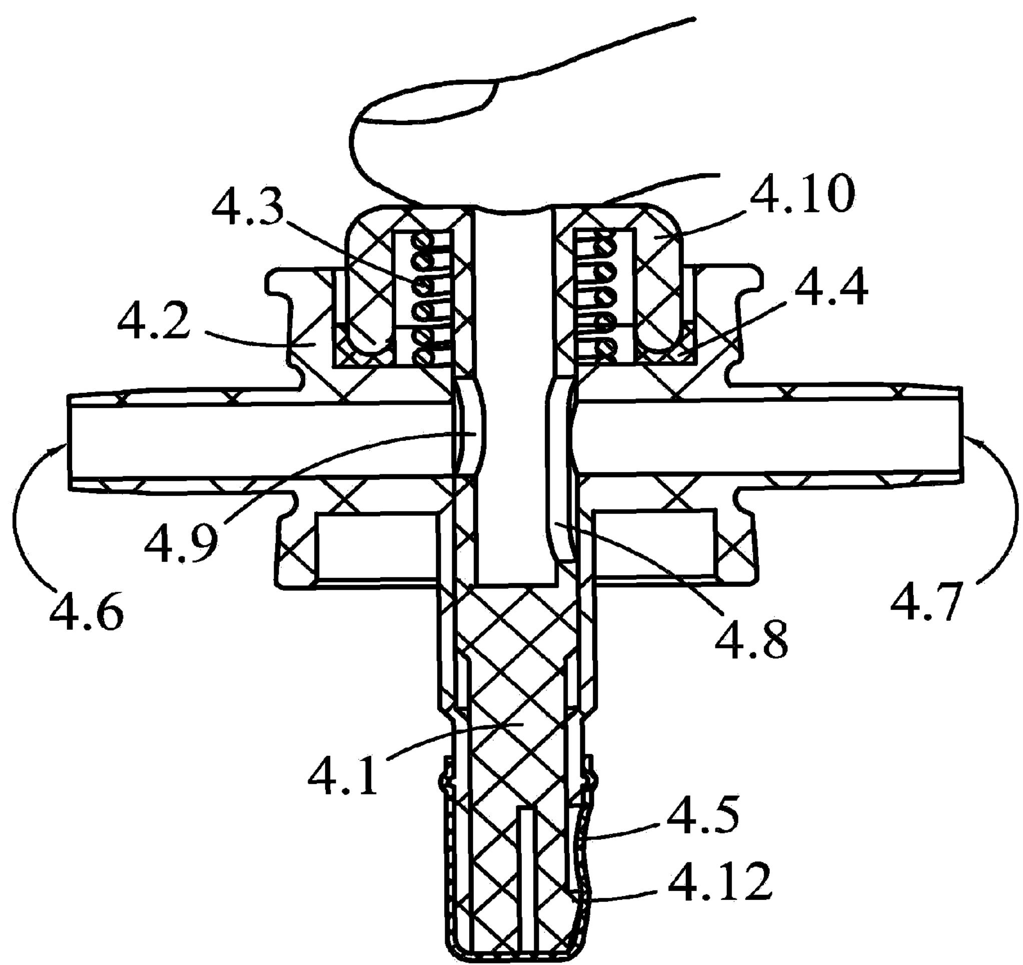
FIG. 4 is another schematic view of a disposable valve disk of the invention.
Figure 5:
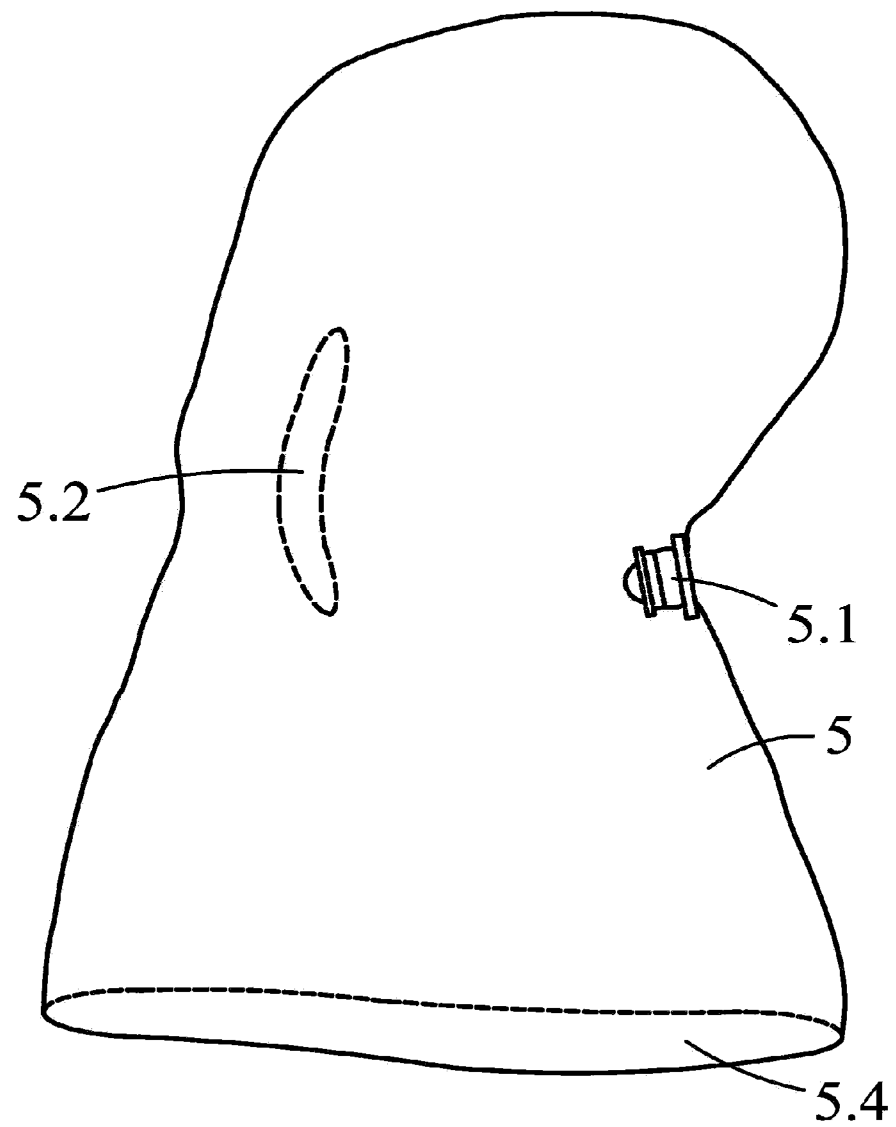
FIG. 5 is a schematic view of a protecting cover of the invention.
Figure 6:
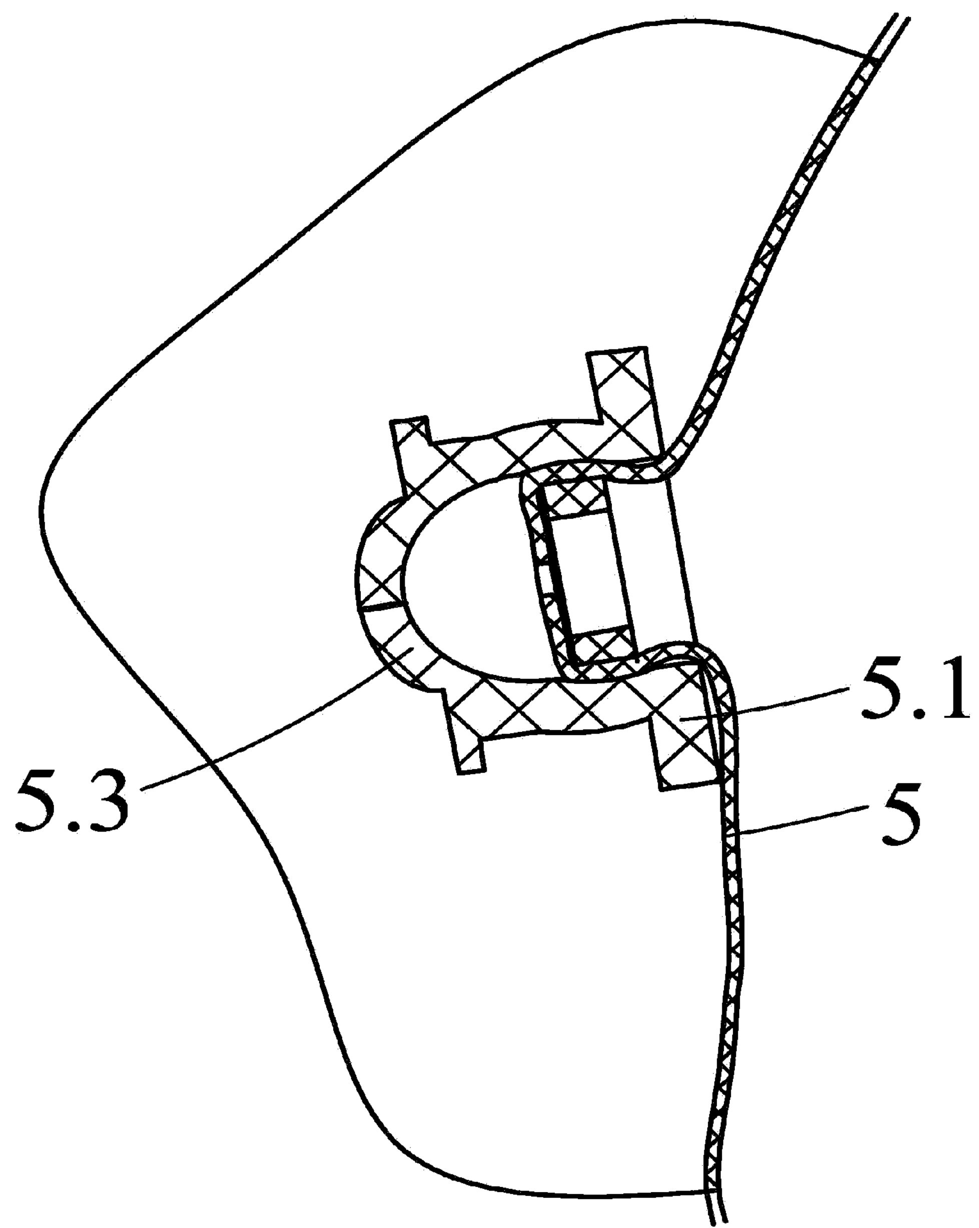
FIG. 6 is a schematic view of an endoscope insertion portion of the invention.
Figure 7:
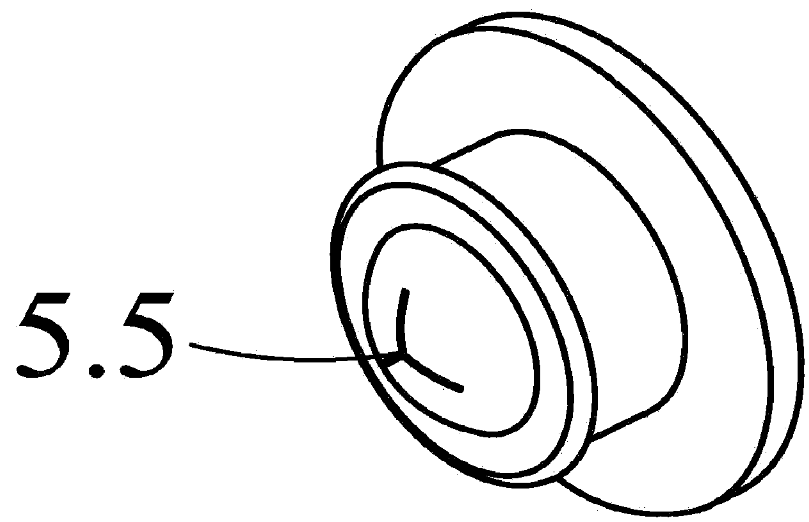
FIGS. 7 and 8 are left views of an instrument insertion opening of the invention.
Figure 8:
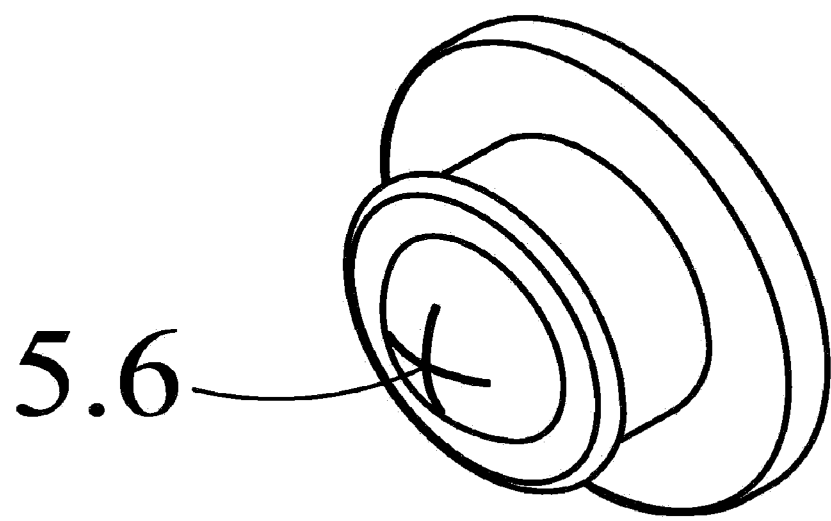
Figure 9:
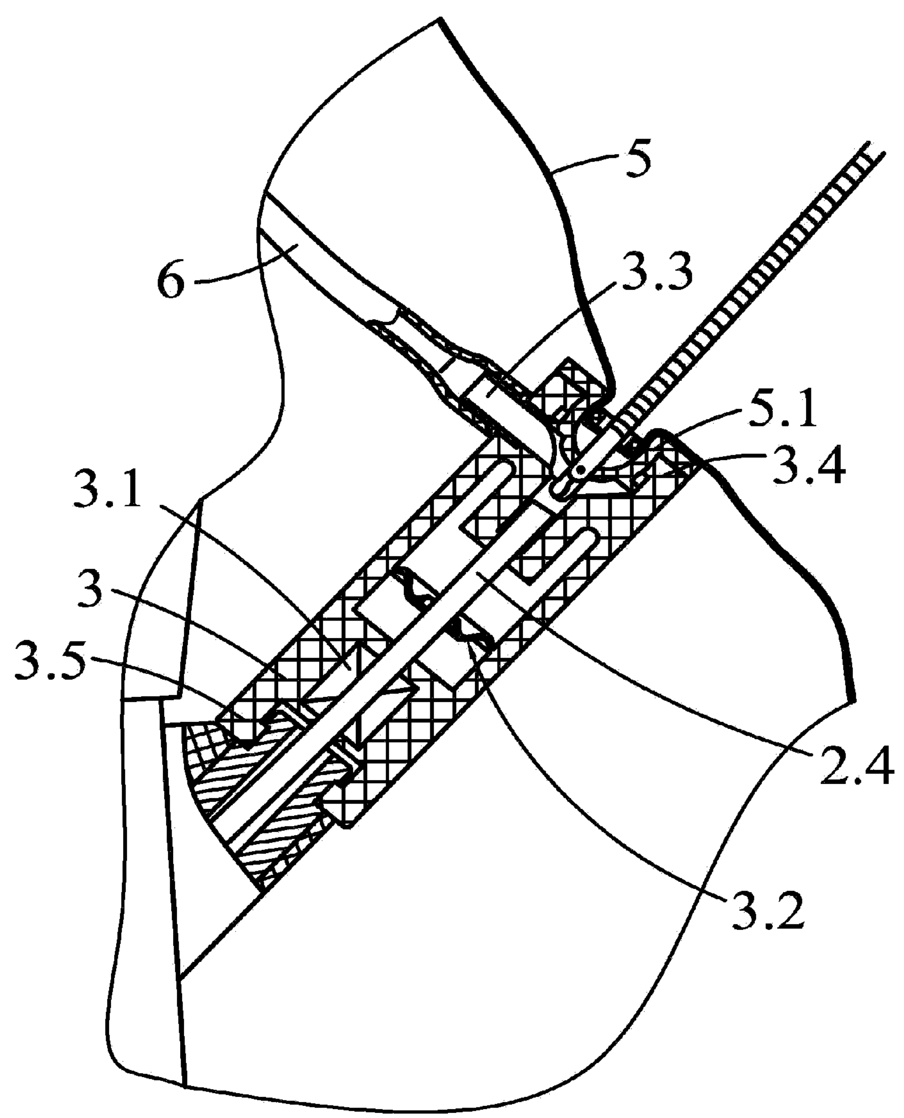
FIG. 9 is a cross-sectional view of an instrument insertion opening and a three-way sealing cap connected altogether.
Figure 10:
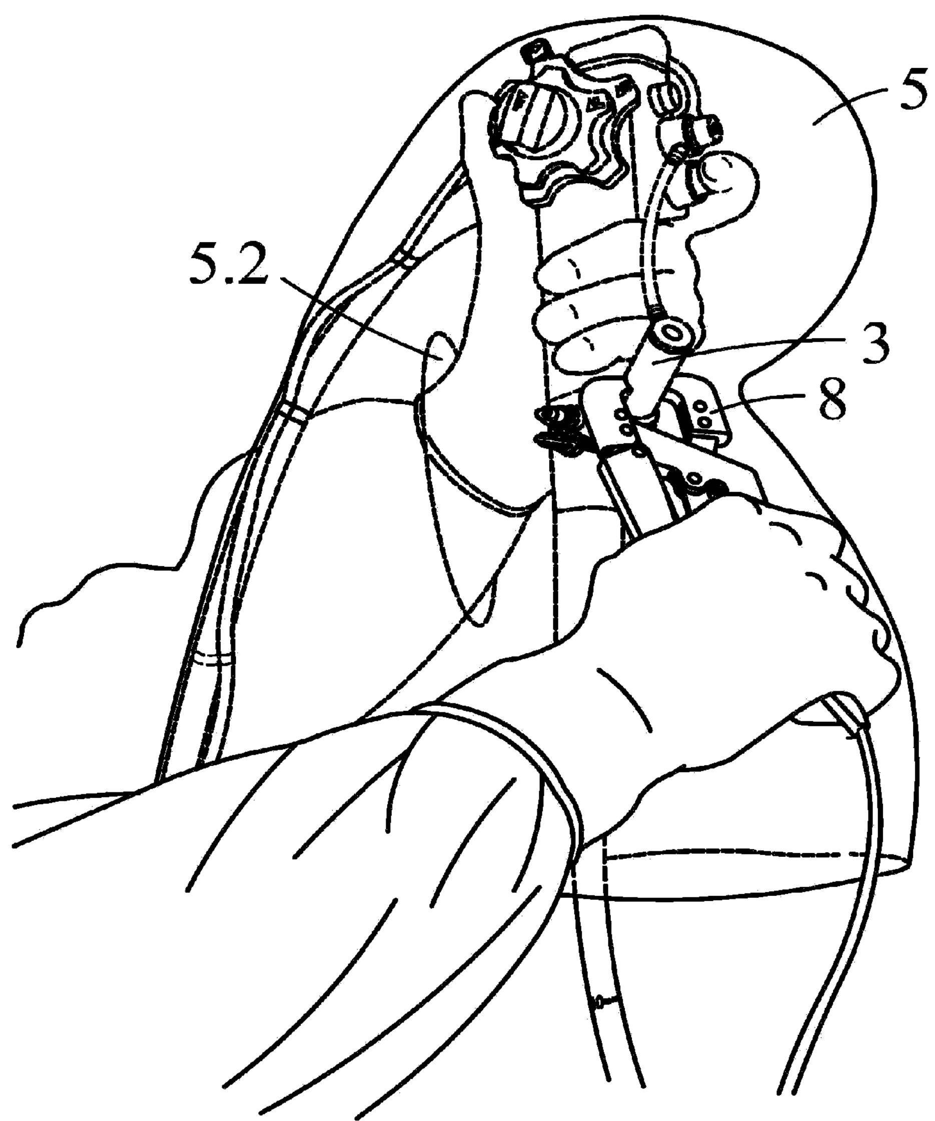
FIG. 10 illustrates heat seal of a heat seal hole from the outside of the protecting cover.

As shown in FIG. 1, a disposable protecting cover of the invention operates to protect a endoscope 1 of an endoscope, and comprises a sheath 2 operating to protect an endoscope insertion portion 1.1 of the endoscope 1. The sheath 2 is made of elastic materials.

A diameter of the sheath 2 is greater than that of the insertion portion.

After the sheath 2 covers the endoscope insertion portion 1.1, a locking ring 2.4 disposed at the back of the sheath 2 is pulled up, at this time a diameter of the sheath 2 is decreased and thickness of a wall thereof is reduced, and the sheath 2 is tightly disposed on outer surface of the endoscope insertion portion 1.1.

A support ring 2.1 is disposed on a front end of the sheath, and a convex portion and a concave portion are respectively disposed on both sides of the support ring 2.1 and fit with a concave portion and a convex portion on a head of the endoscope 1.

Film is disposed on one end of the support ring 2.1, and the transparent film is made of soft and transparent film. An opening is disposed on one end of the film, and connected to an opening disposed in the front of a disposable suction tube 2.3.

A nozzle 2.2 is disposed on one side of the support ring 2.1, and the back of the nozzle 2.2 is connected to a disposable water air tube 2.5.

The disposable water air tube 2.5 is disposed between the sheath 2 and the endoscope 1. A disposable water air connector 2.6 is disposed at the back of the disposable water air tube 2.5, and is fit with an endoscope water air tube connector 1.7 of the endoscope 1. A one-way valve 2.7 is disposed on the disposable water air tube 2.5 and outside the sheath 2 whereby preventing backstreaming of water and air due to variation of pressure in a cavity of a patient.

As the sheath 2 covers the endoscope 1, one end of a disposable suction tube 2.3 passes through an endoscope upper opening 1.5 of the endoscope 1, a length of the disposable suction tube 2.3 being greater than an endoscope channel 1.4 of the endoscope 1, a three-way sealing cap 3 is fit on the disposable suction tube 2.3 by fitting the tube with an awl, and an inner diameter of the three-way sealing cap 3 is less than an outer diameter of the disposable suction tube 2.3.

After the awl is pulled out, an endoscope connector 3.5 of the three-way sealing cap 3 is fixed on the endoscope upper opening 1.5.

A following sealing ring 3.2 is disposed in the three-way sealing cap 3, and operates to prevent the disposable suction tube 2.3 from axially sliding, and dirt at an opening of the disposable suction tube 2.3 from polluting the endoscope channel 1.4. A heat seal hole 3.1 is disposed below the following sealing ring 3.2, and a heat hole forceps 8 operates to cut an unpolluted disposable suction tube 2.3 whereby preventing the disposable suction tube 2.3 from polluting the endoscope channel 1.4 as the disposable suction tube 2.3 is pulled out from the endoscope 1.

A suction tube 6 is disposed outside the endoscope 1 and connected to a suction valve 4. The suction valve 4 is disposable and fit for recycling.

The suction valve 4 comprises a valve seat 4.2, a valve core 4.1, a spring 4.3, a sealing packing 4.4, and a sealing sheath 4.5.

The valve seat 4.2 is disposed in a suction valve seat 1.6 of an operating portion of the endoscope 1. The valve core 4.1 is disposed in the valve seat 4.2. The spring 4.3 and the sealing packing 4.4 are disposed between the valve core 4.1 and the valve seat 4.2. A fixing hook 4.12 is disposed below the valve core 4.1 and operates to fix the valve core 4.1 in the valve seat 4.2. The sealing sheath 4.5 is fit on the bottom of the valve seat 4.2.

A suck-in connector 4.6 and a suck-out connector 4.7 are disposed on both sides of the valve seat 4.2. A long opening 4.8 is disposed on one side of the wall of the valve core 4.1 on which the suck-out connector 4.7 is disposed, and a suck-in hole 4.9 is disposed on the other side thereof.

As a compressing portion 4.10 is pressed or released, an upper central opening of the suck-out connector 4.7 is connected to the long opening 4.8. As the valve core 4.1 is pressed, the suck-in hole 4.9 is connected to the suck-in connector 4.6 of the valve seat 4.2. At this time, an upper central opening 4.11 at the top of the compressing portion 4.10 is already blocked by a finger and starts inhaling. As the compressing portion 4.10 is released, the valve core 4.1 moves upwards as being driven by the spring 4.3, the suck-in hole 4.9 is blocked and stops inhaling. As the finger is moved away from the upper central opening 4.11, air enters from the upper central opening 4.11 via the compressing portion 4.10, and into a liquid-storage bottle of a suction unit via the suction tube 6.

A protecting cover 5 is disposed outside the operating portion 1.2. The protecting cover 5 is in the shape of a cap and made of transparent film.

A hand entrance 5.2 and an instrument insertion opening 5.1 are disposed on the protecting cover 5.

The instrument insertion opening 5.1 is elastically fit with the upper opening 3.4 of the three-way sealing cap 3. An arch-shaped cavity 5.3 is disposed at the center of the instrument insertion opening 5.1 and protrudes inwards. A cut that can be opened is disposed at the center of the arch-shaped cavity 5.3. The cut can be a trisection cut 5.5, a quartering cut 5.6, or employs any other shapes that can implement such functions. As devices are inserted, the cut is opened, and as devices are pulled out, the cut is closed.

As the protecting cover 5 is to be installed, the lower opening 5.4 is downwardly fit on the endoscope operating portion 1.2 and the light guide portion 1.3, and a left hand of an operator enters and holds the operating portion 1.2 for operating via the hand entrance 5.2.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An endoscope system comprising;

an endoscope having an endoscope insertion portion (1.1), an endoscope operation portion (1.2), an endoscope channel (1.4), an endoscope upper opening (1.5), a suction valve seat (1.6), and an endoscope water air tube connector (1.7);

a disposable protecting cover (5) having a hand entrance (5.2), an instrument insertion opening (5.1), and a lower opening (5.4);

a disposable sheath (2); and a disposable channel system comprising:

a disposable suction tube (2.3);

a three-way sealing cap (3);

a suction tube (6);

a water air tube (2.5); and a disposable suction valve (4);

wherein:

said three-way sealing cap (3), said disposable suction valve (4), and a suction unit (A) are attached to one another by said suction tube (6);

said three-way sealing cap (3) and said disposable sheath (2) are attached to one another by said disposable suction tube (2.3);

said endoscope upper opening (1.5), said suction valve seat (1.6), and said endoscope water air tube connector (1.7) are disposed in said endoscope operation portion (1.2);

a bottom part of said endoscope channel (1.4) is disposed in said endoscope insertion portion (1.1), and a top part of said endoscope (1.4) is disposed in said endoscope operation portion (1.2) and connects to said endoscope upper opening (1.5);

said disposable sheath (2) covers said endoscope insertion portion (1.1);

said disposable protecting cover (5) covers portions of the endoscope from top to bottom excluding said endoscope insertion portion (1.1) and covers said endoscope operation portion (1.2);

when said disposable protecting cover (5) is installed, said lower opening (5.4) is downwardly moved such that said disposable protecting cover (5) covers portions of the endoscope from top to bottom excluding said endoscope insertion portion (1.1);

said disposable protecting cover (5) is in the shape of a cap and made of transparent film;

said disposable suction tube (2.3) is placed into said endoscope channel (1.4), passes through said endoscope upper opening (1.5), and enters into a lower opening of a straight cavity of said three-way sealing cap (3);

said lower opening of the straight cavity of said three-way sealing cap (3) is fixed on said endoscope upper opening (1.5);

an upper opening of the straight cavity of said three-way sealing cap (3) is detachably attached to said instrument insertion opening (5.1);

said disposable suction valve (4) is detachably attached to said suction valve seat (1.6) for controlling suction operations of the endoscope;

one end of said water air tube (2.5) is disposed in said disposable sheath (2) and said water air tube (2.5) is disposed between the endoscope and said disposable sheath (2), and the other end of said water air tube (2.5) is attached to said endoscope water air tube connector (1.7);

said disposable suction valve (4) comprises: a valve seat (4.2) having a column having a column bottom part and a column through hole, and a cylinder having a cylinder top end, a cylinder bottom end, a cylinder side wall, a suck-in connecting hole (4.6), and a suck-out connecting hole (4.7); a valve core (4.1) having a core top end, a core side wall, a compressing portion (4.10), an upper central hole with an upper central opening (4.11); a suck-in hole (4.9), and a long opening (4.8), a spring (4.3); and a sealing sheath (4.5);

said suck-in connecting hole (4.6) and said suck-out connecting hole (4.7) are disposed respectively in two opposite portions of said cylinder side wall;

said suck-in connecting hole (4.6) connects with said suction tube (6);

said suck-out connecting hole (4.7) connects with said suction tube (6);

said suck-in hole (4.9) and said long opening (4.8) are disposed respectively in two opposite portions of said core side wall;

said compressing portion (4.10) is disposed at said core top end, said upper central hole is disposed in said core top end, and said upper central opening (4.11) is disposed on the top surface of said compressing portion (4.10);

said upper central hole connects with said suck-in hole (4.9) and said long opening (4.8);

said column is disposed through said cylinder top end and said cylinder bottom end, and said column is fixed to said cylinder;

said column bottom part is detachably attached to said suction valve seat (1.6);

said valve core (4.1) is disposed in said column through hole whereby said long opening (4.8) connects with said suck-out connecting hole (4.7);

said spring (4.3) is disposed between said cylinder top end and said compressing portion (4.10);

said sealing sheath (4.5) is fixed to said column bottom part and seals the bottom opening of said column through hole;

when said compressing portion (4.10) is pressed, said valve core (4.1) moves downward with respect to said valve seat (4.2), said spring (4.3) is pressed, and said sealing sheath (4.5) limits down position of said valve core (4.1);

when said compressing portion (4.10) is released, said spring (4.3) drives said valve core (4.1) to move upward with respect to said valve seat (4.2);

when said compressing portion (4.10) is pressed and when said compressing portion (4.10) is released, said long opening (4.8) connects with said suck-out connecting hole (4.7);

when said compressing portion (4.10) is pressed, said suck-in hole (4.9) connects with said suck-in connecting hole (4.6), and said upper central opening (4.11) is blocked by a finger, whereby suction occurs; and when said compressing portion (4.10) is released, said suck-in hole (4.9) does not connect with said suck-in connecting hole (4.6) whereby suction terminates, and said upper central opening (4.11) is unblocked whereby air enters into said suction unit (A) through said upper central opening (4.11), said upper central hole, said long opening (4.8), said suck-out connecting hole (4.7), and said suction tube (6).

2. The endoscope system of claim 1, wherein an arch-shaped cavity is disposed at the center of said instrument insertion opening.

3. The endoscope system of claim 2, wherein said arch-shaped cavity protrudes inwards.

4. The endoscope system of claim 2, wherein a cut that can be opened is disposed at the center of said arch-shaped cavity.

5. An endoscope system comprising:

an endoscope having an endoscope insertion portion (1.1), an endoscope operation portion (1.2), an endoscope channel (1.4), an endoscope upper opening (1.5), a suction valve seat (1.6), and an endoscope water air tube connector (1.7);

a disposable protecting cover (5) having a hand entrance (5.2), an instrument insertion opening (5.1), and a lower opening (5.4);

a disposable sheath (2); and a disposable channel system comprising:

a disposable suction tube (2.3);

a three-way sealing cap (3);

a suction tube (6);

a water air tube (2.5);

a one-way valve (2.7); and a disposable suction valve (4);

wherein:

said three-way sealing cap (3), said disposable suction valve (4), and a suction unit (A) are attached to one another by said suction tube (6);

said three-way sealing cap (3) and said disposable sheath (2) are attached to one another by said disposable suction tube (2.3);

said endoscope upper opening (1.5), said suction valve seat (1.6), and said endoscope water air tube connector (1.7) are disposed in said endoscope operation portion (1.2);

a bottom part of said endoscope channel (1.4) is disposed in said endoscope insertion portion (1.1), and a top part of said endoscope (1.4) is disposed in said endoscope operation portion (1.2) and connects to said endoscope upper opening (1.5);

said disposable sheath (2) covers said endoscope insertion portion (1.1);

said disposable protecting cover (5) covers portions of the endoscope from top to bottom excluding said endoscope insertion portion (1.1) and covers said endoscope operation portion (1.2);

when said disposable protecting cover (5) is installed, said lower opening (5.4) is downwardly moved such that said disposable protecting cover (5) covers portions of the endoscope from top to bottom excluding said endoscope insertion portion (1.1);

said disposable protecting cover (5) is in the shape of a cap and made of transparent film;

said disposable suction tube (2.3) is placed into said endoscope channel (1.4), passes through said endoscope upper opening (1.5), and enters into a lower opening of a straight cavity of said three-way sealing cap (3);

said lower opening of the straight cavity of said three-way sealing cap (3) is fixed on said endoscope upper opening (1.5);

an upper opening of the straight cavity of said three-way sealing cap (3) is detachably attached to said instrument insertion opening (5.1);

said disposable suction valve (4) is detachably attached to said suction valve seat (1.6) for controlling suction operations of the endoscope;

one end of said water air tube (2.5) is disposed in said disposable sheath (2) and said water air tube (2.5) is disposed between the endoscope and said disposable sheath (2), and the other end of said water air tube (2.5) is attached to said endoscope water air tube connector (1.7);

said disposable suction valve (4) comprises a valve seat (4.2) having a column having a column bottom part and a column through hole, and a cylinder having a cylinder top end, a cylinder bottom end, a cylinder side wall, a suck-in connecting hole (4.6), and a suck-out connecting hole (4.7); a valve core (4.1) having a core top end, a core side wall, a compressing portion (4.10), an upper central hole with an upper central opening (4.11); a suck-in hole (4.9), and a long opening (4.8), a spring (4.3); and a sealing sheath (4.5);

said suck-in connecting hole (4.6) and said suck-out connecting hole (4.7) are disposed respectively in two opposite portions of said cylinder side wall;

said suck-in connecting hole (4.6) connects with said suction tube (6);

said suck-out connecting hole (4.7) connects with said suction tube (6);

said suck-in hole (4.9) and said long opening (4.8) are disposed respectively in two opposite portions of said core side wall;

said compressing portion (4.10) is disposed at said core top end, said upper central hole is disposed in said core top end, and said upper central opening (4.11) is disposed on the top surface of said compressing portion (4.10);

said upper central hole connects with said suck-in hole (4.9) and said long opening (4.8);

said column is disposed through said cylinder top end and said cylinder bottom end, and said column is fixed to said cylinder;

said column bottom part is detachably attached to said suction valve seat (1.6);

said valve core (4.1) is disposed in said column through hole whereby said long opening (4.8) connects with said suck-out connecting hole (4.7);

said spring (4.3) is disposed between said cylinder top end and said compressing portion (4.10);

said sealing sheath (4.5) is fixed to said column bottom part and seals the bottom opening of said column through hole;

when said compressing portion (4.10) is pressed, said valve core (4.1) moves downward with respect to said valve seat (4.2), said spring (4.3) is pressed, and said sealing sheath (4.5) limits down position of said valve core (4.1);

when said compressing portion (4.10) is released, said spring (4.3) drives said valve core (4.1) to move upward with respect to said valve seat (4.2);

when said compressing portion (4.10) is pressed and when said compressing portion (4.10) is released, said long opening (4.8) connects with said suck-out connecting hole (4.7);

when said compressing portion (4.10) is pressed, said suck-in hole (4.9) connects with said suck-in connecting hole (4.6), and said upper central opening (4.11) is blocked by a finger, whereby suction occurs;

when said compressing portion (4.10) is released, said suck-in hole (4.9) does not connect with said suck-in connecting hole (4.6) whereby suction terminates, and said upper central opening (4.11) is unblocked whereby air enters into said suction unit (A) through said upper central opening (4.11), said upper central hole, said long opening (4.8), said suck-out connecting hole (4.7), and said suction tube (6); and said one-way valve (2.7) is disposed on said water air tube (2.5) and is disposed outside said disposable sheath (2).

6. The endoscope system of claim 5, wherein an arch-shaped cavity is disposed at the center of said instrument insertion opening.

7. The endoscope system of claim 6, wherein said arch-shaped cavity protrudes inwards.

8. The endoscope system of claim 6, wherein a cut that can be opened is disposed at the center of said arch-shaped cavity.

* * * * *